United States Patent [19]

Shane et al.

[11] Patent Number: 5,156,629
[45] Date of Patent: Oct. 20, 1992

[54] PNEUMATIC PROSTHETIC INSERT

[76] Inventors: Mark D. Shane, R.R. 2, P.O. Box 93, Wyoming, Ill. 61491; Michelle M. Peters, 1616 Tahoe Circle Dr., Wheeling, Ill. 60090

[21] Appl. No.: 493,691

[22] Filed: Mar. 15, 1990

[51] Int. Cl.$^5$ ................................................ A61F 2/80
[52] U.S. Cl. ...................................... 623/37; 623/901; 128/DIG. 20; 156/242; 156/245
[58] Field of Search ..................................... 623/33–37, 623/901; 128/DIG. 20

[56] References Cited

U.S. PATENT DOCUMENTS

| | | | |
|---|---|---|---|
| 1,057,562 | 4/1913 | LaPoint | 623/37 |
| 2,267,070 | 12/1941 | Baldwin | 128/DIG. 20 X |
| 2,634,424 | 4/1953 | O'Gorman | 623/37 |
| 3,309,714 | 3/1967 | Porten | 623/37 |
| 4,300,245 | 11/1981 | Saunders | 623/37 |

FOREIGN PATENT DOCUMENTS 828140  5/1952  Fed. Rep. of Germany ........ 623/37

OTHER PUBLICATIONS

Improvements in the Air-Cushion Socket for Below-Knee Amputees, Wilson et al., Proceedings of the 2nd International Conference on Rehabilitation Engineering, Ottawa, 1984, pp. 239–240.

Primary Examiner—Ronald Frinks
Attorney, Agent, or Firm—Emrich & Dithmar

[57] ABSTRACT

A removeable and adjustable prosthetic insert disposed between the stump of a limb and the socket of a prosthesis is comprised of a high strength, pliable polymeric material within which are formed a plurality of spaced air pockets, or voids, which are coupled together by a series of connecting channels, or passages. Using an air valve extending through the polymeric material and coupled to the closed air pocket/channel system, the air pockets may be inflated to fill the stump/socket interspace and provide a tight-fitting, air cushioned prosthetic socket attachment. The air inflatable prosthetic insert can accommodate changes in the condition of the stump and applies a uniform prosthetic attaching force thereto. Other embodiments also employ an inflatable air cushion and make use of spaced, solid spheres disposed between air passages arranged in a grid-like array; and pinched tubing with interconnecting air passages to form a series of inflatable nodules. An air cushion isolates the limb stump from the hard, rigid prosthesis socket for user comfort and provides a custom fit for improved control and maneuverability of the prosthetic device.

5 Claims, 7 Drawing Sheets

SECTIONS:
- A (6" DIAMETER)
- B (5" DIAMETER)
- C (4" DIAMETER)

PNEUMATIC PROSTHETIC INSERT

BACKGROUND OF THE INVENTION

This in relates generally to inserts for use with prosthetic devices and is particularly directed to an air inflatable insert worn between a remaining limb and the socket of a prosthetic device.

The fitting of a prosthesis to the remaining stump of an amputated limb such as a leg involves insertion of the stump into a socket of the prosthesis. A spacer, or insert, provides a cushioning effect as well as tight fitting engagement with the prosthesis for the user. Prior art inserts generally suffer from a "piston effect", or relative movement between the stump and prosthesis, which results in irritation of the stump caused by excessive rubbing and pressure spots. Relative movement between the prosthesis and stump also limits control over the prosthesis and restricts user mobility in the case of a leg prosthesis.

Prior art prosthesis inserts take on various forms such as wool stockings or foam rubber attachments. These earlier inserts are formed integrally with the prosthesis or are attached thereto and are thus not removable. In some cases, a wedge-type structure is inserted between the limb stump and prosthesis socket in order to provide a tighter fit. A tight fit eliminates rubbing between the prosthesis and limb stump for improved comfort and reduces the aforementioned "piston effect" for improved prosthesis control. Another source of discomfort are pressure spots caused by contact between the boney and tender parts of the stump and the hard surface of the prosthesis socket. Excessive pressure for extended periods may result in skin ulcerations and infections, particularly for diabetics.

In order to increase comfort and improve control, prosthetic inserts are increasingly designed for individual use. These custom fitted inserts are attached to the prosthesis socket and are uniquely configured for individual use. These custom made inserts, which are not adjustable and expensive to fit, come generally in the form of cloth covered foam pads, air bladders, or fluid filled envelopes. The fluid may be in the form of a free flowing liquid or a gel. While affording a degree of custom fit, fluid filled inserts suffer from leakage problems and offer only a limited improvement in comfort because of the fluid incompressibility.

Air-filled inserts have also suffered from a lack of adjustability of fit and complicated and expensive fabrication procedures. Prior air inflated inserts have also been subject to leakage problems. One example of a pneumatic prosthetic permanent insert is disclosed in an article entitled "Improvement of the Air-Cushion Socket for Below-Knee Amputees" by Wilson et al, published in the Proceedings of the Second International Conference on Rehabilitation Engineering in 1984. This air cushion socket traps a layer of air in a pocket between a lower portion of the socket wall and an elastic sleeve enclosing the limb stump. A cotton loop disposed about the elastic sleeve is inserted in a narrow gap formed by the laminated socket and the distal edge of a brim disposed about the socket for allegedly preventing leakage of the air trapped in the pocket. U.S. Pat. No. 3,309,714 to Porten discloses a pneumatic cushion socket comprised of inner and outer layers of a pliant covering material, with a plastic foam sheeting material disposed between the covering material layers and secured to the inside of the inner wall of the socket. The resilient foam material has minute air spaces therein to permit air introduced under pressure between the inner and outer walls of the socket to fill microscopic interstices within the foam material. Although this approach employs air as a cushion, the primary cushioning effect is provided by the plastic foam sheeting material and thus affords only limited comfort and adjustability.

The present invention overcomes the aforementioned limitations of the prior art by providing a pneumatic prosthetic insert which provides pressure relief and a custom fit for any user of a prosthetic device. The inventive pneumatic prosthetic insert employs air inflatable voids and interconnecting passages disposed between facing inner and outer surface structures. The structure and material of the insert itself do not therefore provide any cushioning effect which is afforded solely by the trapped air.

OBJECTS AND SUMMARY OF THE INVENTION

Accordingly, it is an object of the present invention to provide improved fit and attachment of a prosthetic device to the remaining limb with which it is used.

Another object of the present invention is to provide an adjustable, removable and durable pneumatic prosthetic insert which is also comfortable and affords a high degree of prosthetic control.

A further object of the present invention is to provide a prosthetic insert which is easily installed and removed, inexpensively manufactured, and affords increased user comfort, mobility, security, and safety.

Yet another object of the present invention is to provide secure, tight fitting, cushioned engagement between the remaining limb of an amputee and an artificial limb or prosthesis.

This invention contemplates an inflatable insert for positioning between a stump of a limb and a socket of a prosthetic device, said insert comprising first and second sheet-like pliable structures joined in mutual adherence over a portion of the respective surfaces thereof; means for defining a plurality of voids disposed in a spaced manner intermediate said first and second sheet-like structures; a plurality of air passages disposed intermediate said first and second sheet-like structures and connecting adjacent voids in the insert so as to form a closed network of said air passages and voids; and valve means extending through at least one of said sheet-like structures and into said closed network of air passages and voids to permit the insert to be inflated.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DESCRIPTION OF THE PREFERRED EMBODIMENTS

Figure 1:
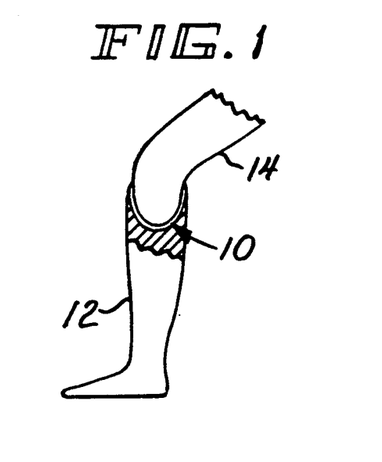
FIG. 1 is a simplified perspective view shown partially cut away of a pneumatic prosthetic insert in accordance with the present invention in position between the stump of a limb and a prosthesis.
Figure 2:
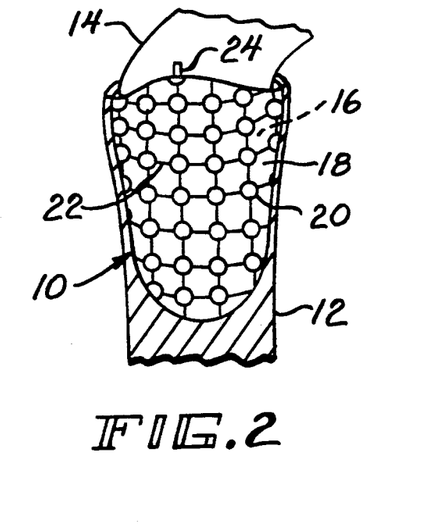
FIG. 2 shows additional details of the pneumatic prosthetic insert of the present invention in position within the socket of a prosthesis.

Referring to FIG. 1, there is shown a partially cutaway perspective view of a pneumatic prosthetic insert 10 in accordance with the present invention. FIG. 2 shows additional details of the inventive pneumatic prosthetic insert 10 positioned between a prosthetic device 12 and a remaining limb, or stump, 14. The pneumatic prosthetic insert 10 is adapted for positioning within the socket of a prosthesis 12 and for receiving the end of a remaining limb 14. The pneumatic prosthetic insert 10 is a valve adjustable, inflatable appliance worn by an amputee which reduces friction and associated discomfort and pain by providing a thin air cushion between the skin of the limb and a hard, rigid prosthesis socket. The pneumatic prosthetic insert 10 also provides a custom fit for the amputee and thus affords improved prosthesis control and mobility for the user. In addition, the pneumatic prosthetic insert 10 fills up the limb prosthesis interspace that inevitably forms due to limb atrophy. The inflatable nature of the pneumatic prosthetic insert 10 of the present invention as well as its use of a thin structure comprised of a highly flexible material affords a custom fit for the user as well as adjustability to allow for bodily changes that occur with time.

Figure 3:
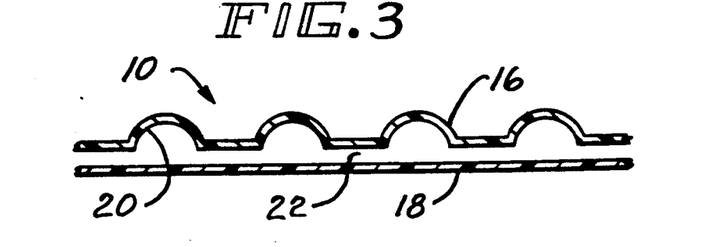
FIG. 3 is a sectional view of a portion of a pneumatic prosthetic insert in accordance with the principles of the present invention.

As shown in FIG. 2, as well as in the sectional view of FIG. 3, the pneumatic prosthetic insert 10 is comprised of a first inner wall 16 and a second outer wall 18. Each of these walls 16, 18 is preferably comprised of a tough, wear resistant, flexible material which is resistant to moisture and not subject to stretching. A preferred embodiment of the pneumatic prosthetic insert 10 contemplates the use of a polymeric material for forming the inner and outer walls thereof. The inner and outer walls 16, 18 are joined along portions thereof and are configured so as to form a plurality of spaced voids, or chambers, 20 interconnected by a series of air passages, or channels, 22. The spaced array of voids 20 within the pneumatic prosthetic insert 10 are similar to those found in bubbled, packing material used to protect fragile items. The insert 10 may be formed as a generally flat sheet or in the form of a sock as described below. The sock is adapted to receive the end of a remaining limb, while the pneumatic prosthetic insert 10 in sheet form is adapted for wrapping around the remaining limb prior to insertion in the socket of a prosthetic device. The interconnected voids 20 and air passages 22 form a continuous, closed network which can be inflated by means of a valve 24 inserted through the insert's wall and into one of the aforementioned voids 20 or passages 22. The valve 24 permits the pneumatic prosthetic insert 10 to be inflated to a suitable pressure.

In one embodiment, the pneumatic prosthetic insert 10 is in the form of a generally flat sheet, on the order of 0.01 inch thick and six inches on each side with each air passage 22 being 0.125 inch in diameter and 0.75 inch in length. Each of the air chambers 20 has a radius of approximately 0.4375 inch. The valve 24 may be conventional in design and permits the pneumatic prosthetic insert 10 to be inflated, while retaining air therein during use. The valve 24 may thus be of the type which is adapted to receive an air pump-connected pin such as used in footballs, basketballs, etc. The valve 24 may also be of the type used in inner tubes and may be positioned between adjacent portions of the first inner and second outer walls 16, 18 during fabrication of the pneumatic prosthetic insert 10. The valve 24 may also be in the form of a flexible hollow tube which may be crimped or bent or tied off to prevent the escape of air following inflation of the insert.

The first inner and second outer walls 16, 18 are joined along the adjacent edges thereof as well as inner portions thereof by conventional means such as by heat sealing or the use of an adhesive such as an epoxy cement. The polymeric material contemplated for use in a preferred embodiment of the pneumatic prosthetic insert 10 is comprised of a thin layer of polyvinyl chloride (PVC) which is a thermoplastic material which can be heat-sealed by the application of radiant heat.

Figures 4A, 4B:
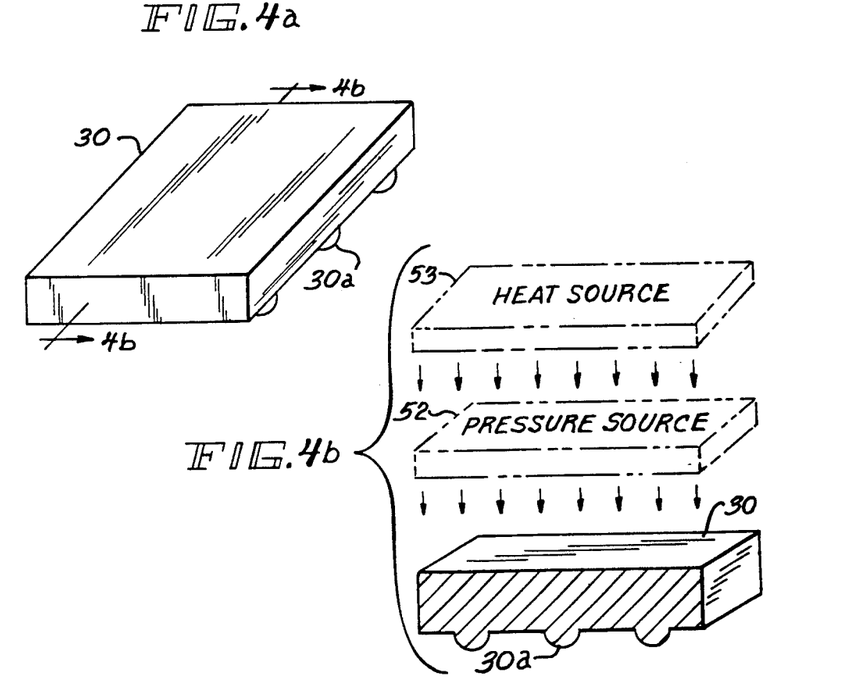
FIGS. 4a and 4b are combined sectional and perspective views of a male compression mold for forming the pneumatic prosthetic insert of the present invention.
Figure 5A:
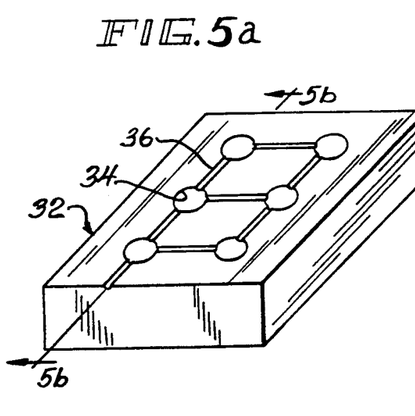
FIGS. 5a and 5b are combined sectional and perspective views of a female compression mold for use with the male compression mold of FIGS. 4a and 4b in forming a pneumatic prosthetic insert in accordance with the present invention.
Figure 5B:
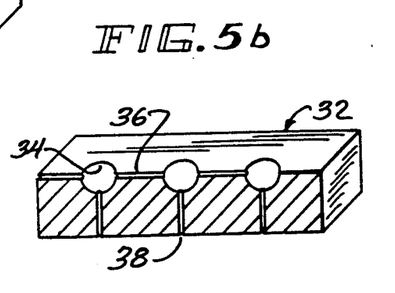
Figure 6A:
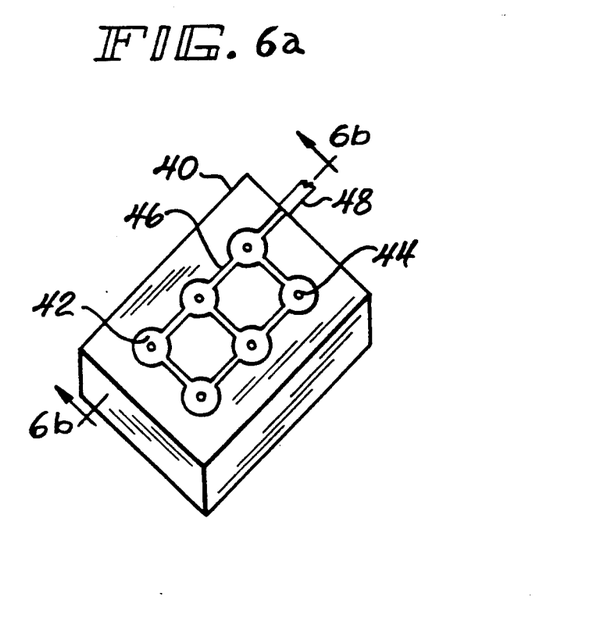
FIGS. 6a and 6b are combined sectional and perspective views of a vacuum mold for use in forming the pneumatic prosthetic insert of the present invention.
Figure 6B:
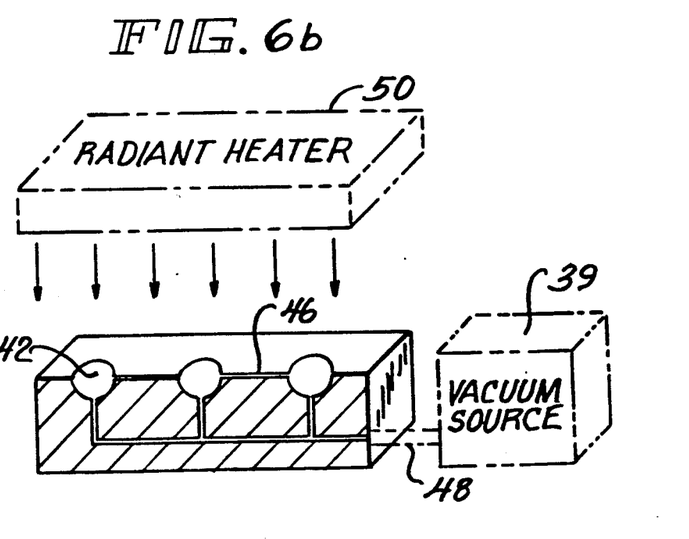
Figure 7A:
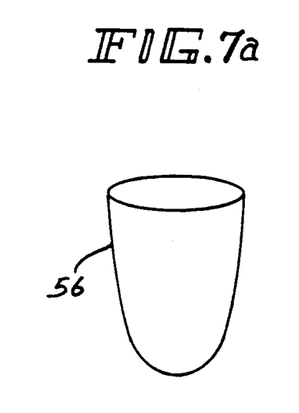
FIGS. 7a–7g illustrates a series of steps in molding a pneumatic prosthetic insert in accordance with the present invention.
Figure 7B:
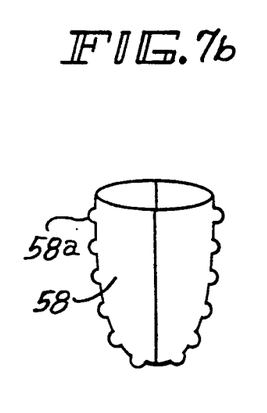
Figure 7C:
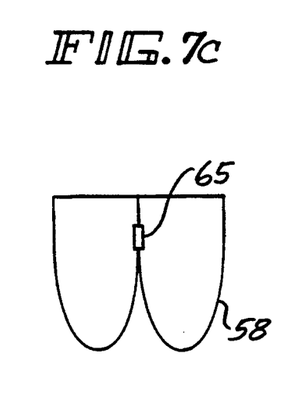
Figure 7D:
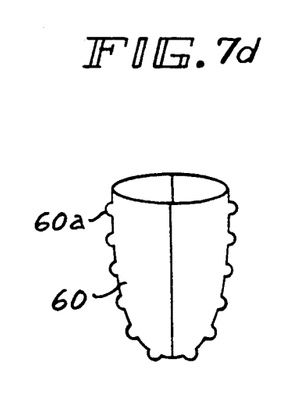
Figure 7E:
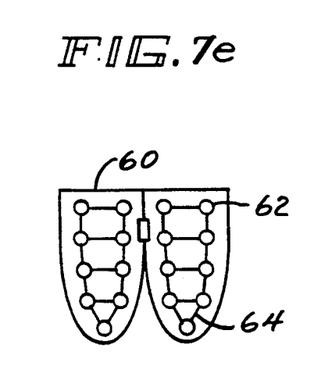
Figure 7F:
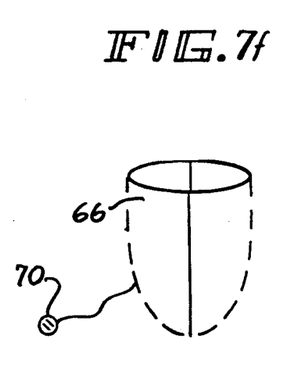
Figure 7G:
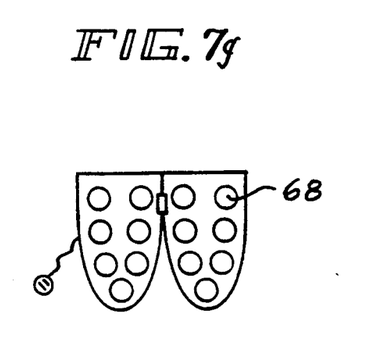

Referring to FIGS. 4a, 4b and 5a, 5b, there are respectively shown perspective views of upper and lower compression mold members 30 and 32 for forming the pneumatic prosthetic insert of the present invention. As shown in FIGS. 4a and 4b, the upper compression mold member 30 includes a series of spaced projections 30a on a lower surface thereof. The upper mold member 30 thus corresponds to the male half of the compression mold. As shown in FIGS. 6a and 6b, an upper surface of the lower mold member 32 is provided with a plurality of spaced recesses 34. Adjacent pairs of recesses 34 are coupled by means of air passages 36. The projections 30a on the upper mold member 30 and the recesses 34 within the lower mold member 32 are generally hemispherical in shape. The air passages 36 are generally semicircular in cross section. Extending downward from each of the recesses 34 within the lower mold member 32 is a respective air vent 38.

The pneumatic prosthetic insert is formed by the compression mold shown in FIGS. 4a, 4b and 5a, 5b in the following manner. A sheet of polymeric material is positioned on the upper surface of the lower mold member 32 and the upper and lower mold members are positioned in tight fitting, abutting contact with the raised solid projections 30a on the upper mold member inserted in the hemispherical recesses 34 in the lower mold member. The sheet of polymeric material is thus placed over the entire upper surface of the lower mold member 32, including the recesses 34 and air passages 36 therein and the two mold members are pressed together by a moveable pressure source 52 and heat is applied by a heat source 53. This forces air from the recesses 34 and air passages 36 in the lower mold member 32 which also includes elongated linear projections (not shown for simplicity) which fit into each of the air passages. The polymeric sheet thus assumes the contour of the upper surface of the lower mold member 32. A second sheet of polymeric material is then positioned on the first sheet of polymeric material and is affixed thereto either by an adhesive or by hot rolling or other conventional bonding technique. The resulting structure is comprised of the upper and lower sheets of polymeric material with a series of spaced hemispherical recesses disposed therebetween and interconnected by a series of air passages 36. The advantage of the compression mold approach just described is that it provides a highly uniform thickness in the pneumatic prosthetic insert. In addition, the two-part compression mold is relatively easy and inexpensive to fabricate as well as to use in forming the two layered pneumatic prosthetic insert.

Referring to FIGS. 6a and 6b, there is shown another apparatus for forming a pneumatic prosthetic insert in accordance with the present invention. The apparatus of FIGS. 6a and 6b includes a vacuum mold 40 having a plurality of uniformly spaced cavities 42 and connecting air passages 46 located on the upper surface of the mold. Small vacuum ducts 44 are drilled in each of the cavities 42 and extend to the lower surface of the vacuum mold 40. These vacuum ducts 44 are coupled to and continuous with a central vacuum tube 48 which extends through the vacuum mold 40. A radiant heater 50 is positioned above a thin sheet of polymeric material disposed on the upper surface of the vacuum mold 40. The radiant heater 50 heats the sheet of polymeric material to its glass transition temperature, whereupon a vacuum is applied by a vacuum source 39 via the vacuum tube 48 and vacuum ducts 44 to draw the sheet of polymeric material into the cavities 42 and over the air passages 44. Another sheet of polymeric material is then bonded to the upper, planar surface of the first sheet of the finished molded material by means of adhesives or hot rolling to form a pneumatic prosthetic insert in accordance with the present invention. The pneumatic prosthetic insert formed by the compression and vacuum molding techniques of FIGS. 4a, 4b, 5a, 5b, 6a and 6b includes a flat surface and a surface with a plurality of spaced projections extending therefrom. When worn, the flat surface is positioned in contact with the limb stump for increased comfort. The advantages of the vacuum mold approach shown in FIGS. 6a and 6b are in the relatively straight forward design and fabrication of the vacuum mold as well as its low cost, and the ease of the vacuum molding process.

Referring to FIG. 7, there is shown a four step molding process representing yet another approach in forming a pneumatic prosthetic insert in accordance with the present invention. The pneumatic prosthetic insert formed by the methods illustrated in FIGS. 4a, 4b and 5a, 5b as well as in FIGS. 6a and 6b is in the form of a flat sheet comprised of upper and lower layers of a polymeric or plastic material. The flat sheet thus formed can then be shaped in the form of a sock so as to tightly fit about and encompass the end of a limb stump. The thus formed insert necessarily includes a seam extending through a portion of the insert. The four step molding process shown in FIG. 7 forms a seamless pneumatic prosthetic insert which more tightly fits and conforms to the shape of the limb stump and which provides a uniform cushion about the entire periphery of the stump. In the process illustrated in FIG. 7, a smooth inner mold 56 is wrapped with a polymeric material which is not shown in the figure for simplicity. With the polymeric material wrapped around the smooth inner mold 56, this combination is inserted into the open upper portion of a second inside mold 58 which is provided with a plurality of spaced projections 58 extending outward therefrom. As shown in the inner projection view of the second inside mold 58, its inner surface is smooth. A second sheet of polymeric material is then wrapped around the outer surface of the second inside mold 58, with the combination of the second inside mold 58 and the first inner mold 56 then placed inside a third outside mold 60. The third outside mold 60 is also open at the top and includes a plurality of projections 60a extending outward therefrom. Each of these projections 60a forms a cavity 62 on the inner surface of the third outside mold 60, with adjacent cavities coupled by means of channels 64. The entire assembly is then positioned within a heating element 66 which is open at the top and includes a plurality of spaced cavities 68 therein each adapted to receive a respective one of the projections 60a on the outer surface of the third outside mold 60. The heating element 66 is coupled to a power source 70 and applies heat to the two sheets of polymeric material respectively disposed about the first inner mold 56 and the second inside mold 58.

Each of the aforementioned molds is comprised of two complementary half portions which may be separated such as by means of a hinge coupling 65 to permit the various molds to be opened and the two sheets of polymeric material to be removed. The smooth first sheet is then positioned within the bubbled second sheet and the two sheets are bonded together by heat sealing or an adhesive as previously described.

Figure 8A:
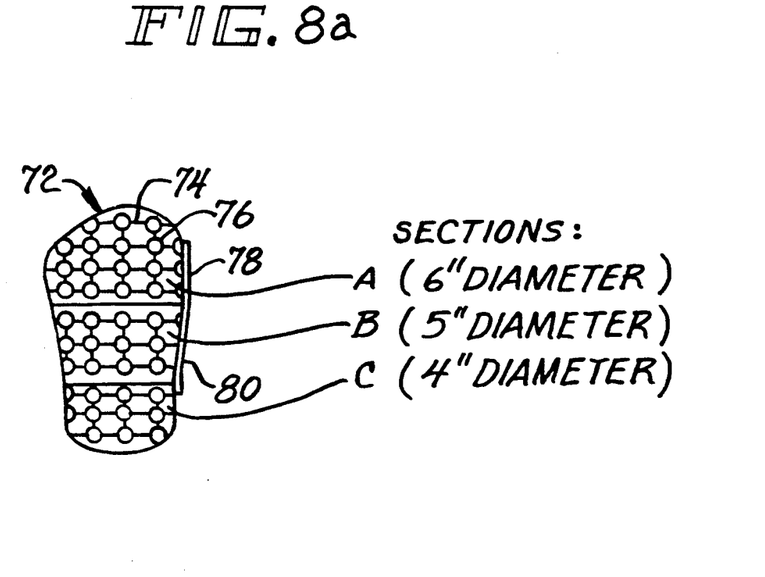
FIGS. 8a and 8b are respectively side and back views of a pneumatic prosthetic insert in accordance with the present invention.
Figure 8B:
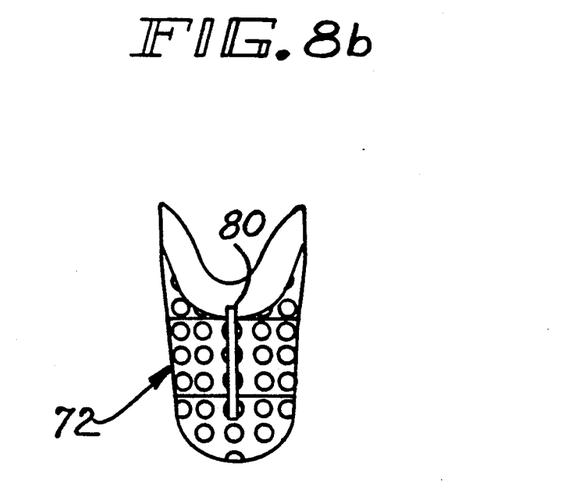

Referring to FIGS. 8a and 8b, there are respectively shown side and back views of a pneumatic prosthetic insert 72 in accordance with the present invention. As described previously, the pneumatic prosthetic insert 72 includes a plurality of spaced air chambers 76 coupled together by a network of air passages 74. Disposed on a rear portion of the pneumatic prosthetic insert 72 is a seam with an air coupling hose 80. The air coupling hose 80 is coupled to and continuous with the network of air chambers 76 and air passages 74 within the pneumatic prosthetic insert 72 and permits inflation and deflation of the insert via a valve stem 78 extending upward from the air coupling hose. As indicated above, the valve employed in the pneumatic prosthetic insert 72 may take on various forms, including a bendable hose which permits the insert to be blown up by mouth and which can be tightly folded or tied to prevent escape of the air and maintain the insert inflated. FIG. 8a includes typical dimensions of a pneumatic prosthetic insert for use by a person of generally average size.

Figure 9A:
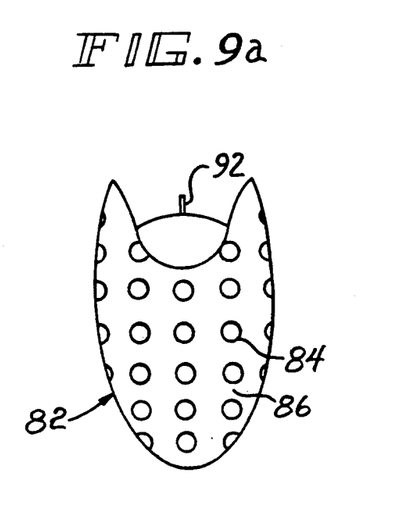
FIGS. 9a and 9b are respectively front and side views of another embodiment of a pneumatic prosthetic insert in accordance with the principles of the present invention.
Figure 9B:
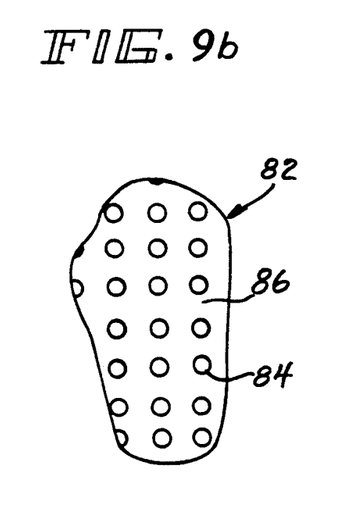
Figure 10:
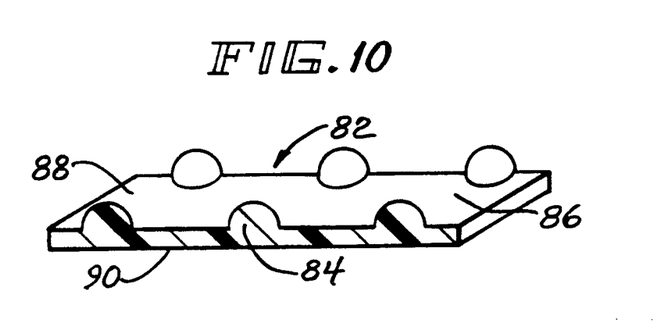
FIG. 10 is a perspective view of a portion of the pneumatic prosthetic insert illustrated in FIGS. 9a and 9b.

Referring to FIGS. 9a and 9b, there are respectively shown front and side views of yet another embodiment of a pneumatic prosthetic insert 82 in accordance with the present invention. A perspective view of the pneumatic prosthetic insert 82 is shown in FIG. 10. The pneumatic prosthetic insert 82 includes first and second spaced walls 88, 90, with a plurality of spaced solid spheres 84 disposed between the two walls. The first and second walls 88, 90 are preferably comprised of a polymeric material and are affixed to opposed portions of each of the solid spheres 84. Attachment of the walls 88, 90 to the solid spheres 84 may be by conventional adhesive means or heat sealing techniques well known to those skilled in the relevant arts.

The solid spheres 84 are preferably comprised of a compressible material such as foam rubber. The spaced arrangement of the first and second walls 88, 90 afforded by the solid spheres 84 forms a series of air passages 86 between the walls and in the space between adjacent spheres. The air passages 86 may be inflated by means of an air valve 92. The pliant nature of the first and second walls 88, 90 permits a pneumatic prosthetic insert 82 to receive a limb stump in tight fitting relation, while the compressible solid spheres 84 as well as the inflated air passages 86 provide compressibility for increased user comfort. The embodiment of the pneumatic prosthetic insert 82 is easily manufactured and does not require a mold or a molding procedure.

Figure 11A:
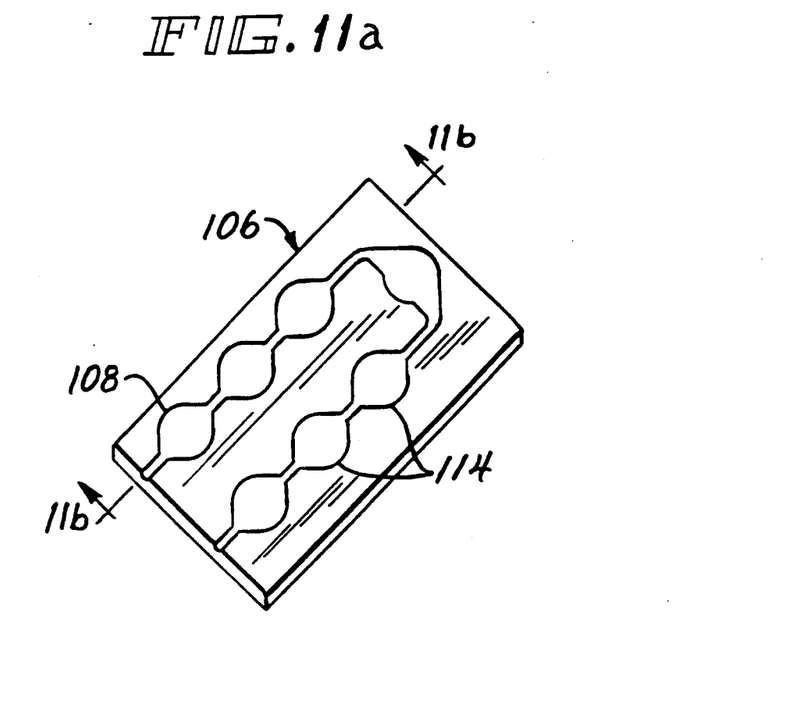
FIGS. 11a and 11b are perspective and sectional views, respectively, of a portion of another embodiment of a pneumatic prosthetic insert in accordance with the present invention.
Figure 11B:
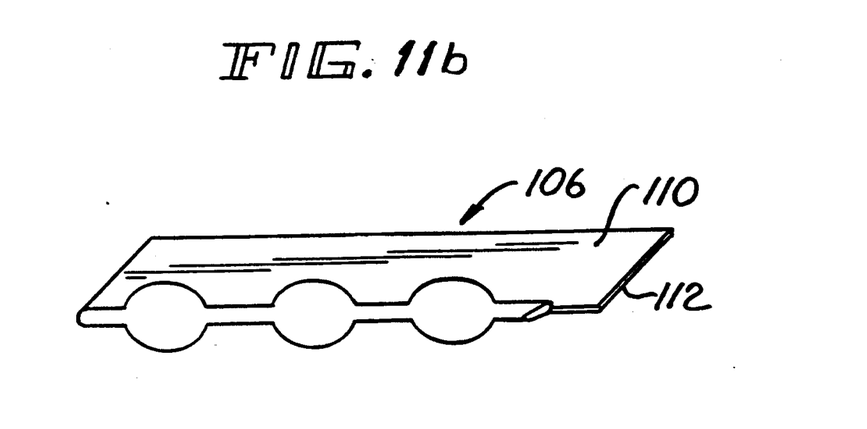

Referring to FIGS. 11a and 11b, there is shown yet another embodiment of a pneumatic prosthetic insert 106 in accordance with the present invention. The pneumatic prosthetic insert 106 is comprised of thermal shrink tubing 108 to which heat and pressure are applied uniformly to form a plurality of nodules 114 within and along the length of the shrink tubing. The shrink tubing 108 is then arranged in the form of a sock-shaped prosthetic insert. First and second sheets 110, 112 of a shrink wrap material are then applied to opposing sides of the shrink tubing to maintain the prosthetic insert shape. A valve (not shown) is provided for inflating the multi-nodule shrink tubing 108. Conventional shrink tubing and shrink wrap materials may be used in forming the pneumatic prosthetic insert 106. This latter embodiment of a pneumatic prosthetic insert also offers the advantages of ease of manufacture at a low cost.

There has thus been shown a pneumatic prosthetic insert which is easily and inexpensively manufactured and which affords the user a high degree of comfort and control over the prosthetic device. The pneumatic prosthetic insert includes a plurality of spaced air channels connecting adjacent air chambers to form a closed inflatable network to which air may be added or removed via a conventional air valve. The pneumatic prosthetic insert relies entirely upon air pressure for attachment to and control over a prosthetic device which permits the insert to be custom fitted to virtually any size or shape of remaining limb stump.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. An inflatable insert for positioning between a stump of a limb and a socket of a prosthetic device, said insert comprising:

first and second sheet-like, pliable structures joined in mutual adherence over a portion of the respective surfaces thereof and forming a generally flat structure adapted for wrapping around the stump of a limb, wherein said first sheet-like, pliable structure is generally planar and said second sheet-like, pliable structure includes a plurality of projections extending outward therefrom;

means for defining a plurality of hemispherically shaped voids disposed in a spaced manner intermediate said first and second sheet-like structures, wherein each of said projections on said second sheet-like, pliable structure corresponds to a respective one of the voids disposed intermediate the first and second sheet-like structures;

a plurality of elongated, tube-like air passages disposed intermediate said first and second sheet-like structures and connecting adjacent voids in the insert so as to form a closed network of said air passages and voids; and valve means extending through at least one of said sheet-like structures and into said closed network of air passages and voids to permit the insert to be inflated.

2. The inflatable insert of claim 1 wherein each of said first and second sheet-like pliable structures is comprised of a polymeric material.

3. The inflatable insert of claim 1 wherein the insert is in the form of a receptacle open at the top for receiving the stump of a limb.

4. The inflatable insert of claim 1 wherein said plurality of air passages and said means for defining the plurality of voids comprises shrink tubing to which pressure and heat are simultaneously applied in a spaced manner along the length thereof to form a series of nodules coupled by air passages along the length of said shrink tubing.

5. An inflatable insert for use with a prosthetic device, said insert comprising:

receptacle means open at the top and closed at the bottom and having inner and outer sheet-like, pliable structures joined in mutual adherence over facing adjacent portions thereof for receiving a stump of a limb, wherein said outer sheet-like, pliable structure is generally smooth and said inner sheet-like, pliable structure includes a plurality of hemispherically shaped projections extending outward therefrom;

first means defining a plurality of spaced voids intermediate the inner and outer sheet-like, pliable structures of said receptacle means, wherein aid voids are formed by the plurality of hemispherically shaped projections on said inner sheet-like, pliable structure;

second means disposed intermediate said inner and outer sheet-like, pliable structures for forming elongated, tube-like air passages between adjacent hemispherically shaped voids in said receptacle means in forming a closed network of air passages and voids; and valve means coupled to said closed network to permit the inflation of the insert when positioned within a socket of a prosthetic device.

* * * * *

UNITED STATES PATENT AND TRADEMARK OFFICE
CERTIFICATE OF CORRECTION

PATENT NO. : 5,156,629

DATED : October 20, 1992

INVENTOR(S) : Mark D. Shane et al.

It is certified that error appears in the above-identified patent and that said Letters Patent is hereby corrected as shown below:

COLUMN    LINE 1         5        "in" should be --invention--.

8         54       "aid" should be --said--.

Signed and Sealed this

Twenty-eighth Day of September, 1993

Attest:

BRUCE LEHMAN

Attesting Officer

Commissioner of Patents and Trademarks